(12) United States Patent
Massarwi et al.

(10) Patent No.: US 12,558,014 B2
(45) Date of Patent: Feb. 24, 2026

(54) SYSTEMS AND METHODS FOR CARDIAC CHAMBER VISUALIZATION

(71) Applicant: Biosense Webster (Israel) Ltd., Yokneam (IL)

(72) Inventors: Fady Massarwi, Baka Al Gharbiyya (IL); Assaf Cohen, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 354 days.

(21) Appl. No.: 17/022,941

(22) Filed: Sep. 16, 2020

(65) Prior Publication Data

US 2022/0079462 A1 Mar. 17, 2022

(51) Int. Cl.
*A61B 5/00* (2006.01)
*A61B 5/055* (2006.01)
(Continued)

(52) U.S. Cl.
CPC ............ *A61B 5/339* (2021.01); *A61B 5/0084* (2013.01); *A61B 5/055* (2013.01); *A61B 5/061* (2013.01);
(Continued)

(58) Field of Classification Search
CPC ....... A61B 5/339; A61B 5/0084; A61B 5/055; A61B 5/061; A61B 5/349; A61B 5/0013;
(Continued)

(56) References Cited

U.S. PATENT DOCUMENTS 6,556,695 B1 * 4/2003 Packer ................. G01R 33/563
382/128
11,406,845 B2 * 8/2022 Robinson ............... A61B 6/503
(Continued)

FOREIGN PATENT DOCUMENTS

AU 2007237321 A1 * 6/2008 ............. A61B 34/20
EP 3102141 A1 * 12/2016 ......... A61B 1/00009
(Continued)

OTHER PUBLICATIONS

William R. Scott, Gerhard Roth, and Jean-François Rivest. 2003. View planning for automated three-dimensional object reconstruction and inspection. ACM Comput. Surv. 35, 1 (Mar. 2003), 64-96. https://doi.org/10.1145/641865.641868 (Year: 2003).*
(Continued)

*Primary Examiner* — Michael J Carey
*Assistant Examiner* — Zainab Mohammed Aldarraji
(74) *Attorney, Agent, or Firm* — Volpe Koenig

(57) ABSTRACT

A system and method for visualizing a cardiac structure of interest including at least one imaging device that obtains image data of a cardiac structure of interest from within the cardiac structure, and a processor comprising a memory The processor is configured to receive and store model data of the cardiac structure of interest, determine at least one location for positioning the at least one imaging device within the cardiac structure of interest to obtain image data of the cardiac structure of interest, receive the image data from the at least one imaging device positioned at the at least one determined location within the cardiac structure of interest, and generate a 3D electrophysiological map of the cardiac structure of interest from within the electrophysiological map.

20 Claims, 12 Drawing Sheets

(51) Int. Cl.

| | |
|---|---|
| *A61B 5/06* | (2006.01) |
| *A61B 5/339* | (2021.01) |
| *A61B 5/349* | (2021.01) |
| *G06T 7/00* | (2017.01) |
| *G06T 17/20* | (2006.01) |
| *A61B 5/283* | (2021.01) |
| *A61B 6/50* | (2024.01) |
| *A61B 8/08* | (2006.01) |

(52) U.S. Cl.
CPC ............ *A61B 5/349* (2021.01); *G06T 7/0012* (2013.01); *G06T 17/20* (2013.01); *A61B 5/0013* (2013.01); *A61B 5/283* (2021.01); *A61B 6/503* (2013.01); *A61B 8/0883* (2013.01); *G06T 2207/30048* (2013.01)

(58) Field of Classification Search
CPC ....... A61B 5/283; A61B 6/503; A61B 8/0883; A61B 2017/00053; A61B 2034/105; A61B 90/361; A61B 2576/023; A61B 5/742; A61B 5/367; G06T 7/0012; G06T 17/20; G06T 2207/30048; G06T 2210/41; G06T 19/00
See application file for complete search history.

(56) References Cited

U.S. PATENT DOCUMENTS

| | | | |
|---|---|---|---|
| 2005/0014995 A1 | 1/2005 | Amundson |
| 2006/0159323 A1 | 7/2006 | Sun et al. |
| 2012/0039526 A1 | 2/2012 | Garaas |
| 2013/0079645 A1 | 3/2013 | Amirana |
| 2014/0343408 A1 | 11/2014 | Tolkowsky |
| 2017/0238807 A9 | 8/2017 | Vertikov |
| 2018/0256056 A1* | 9/2018 | Lu ........................... A61B 5/319 |
| 2018/0279954 A1* | 10/2018 | Hayam ................... G16H 50/50 |

FOREIGN PATENT DOCUMENTS

| | | |
|---|---|---|
| WO | 2016/210437 A1 | 12/2016 |
| WO | WO-2019055115 A1 * | 3/2019 ........... A61B 5/0245 |

OTHER PUBLICATIONS

@inproceedings{Marzal2012TheTA, title={The three-dimensional art gallery problem and its solutions}, author={Jefri Marzal}, year={2012} (Year: 2012).*

O'Rourke, Joseph, "Art Gallery Theorems And Algorithms," New York, Oxford University Press, Inc. (1987).

Csizmadia, et al., "Note On Art Gallery Problem," Computational Geometry, vol. 10, p. 47-55 (1998).

Marzal, Jefri, "The Three-Dimensional Art Gallery Problem And Its Solutions," Murdoch University School of Information Technology (2012).

Tagliasacchi, et al., "Mean Curvature Skeletons," Computer Graphics Forum (Proceedings of the Symposium on Geometry Processing), 31(5):1735-1744 (2012).

European Search Report for corresponding EPA No. 21196741.9 dated Jan. 2, 2022.

Communication pursuant to Article 94(3) EPC issued on Dec. 2, 2024 for European Patent Application No. 1 21196741.9.

Japanese Office Action dated Jul. 15, 2025 for Japanese Patent Application No. 2021-149986.

* cited by examiner

500

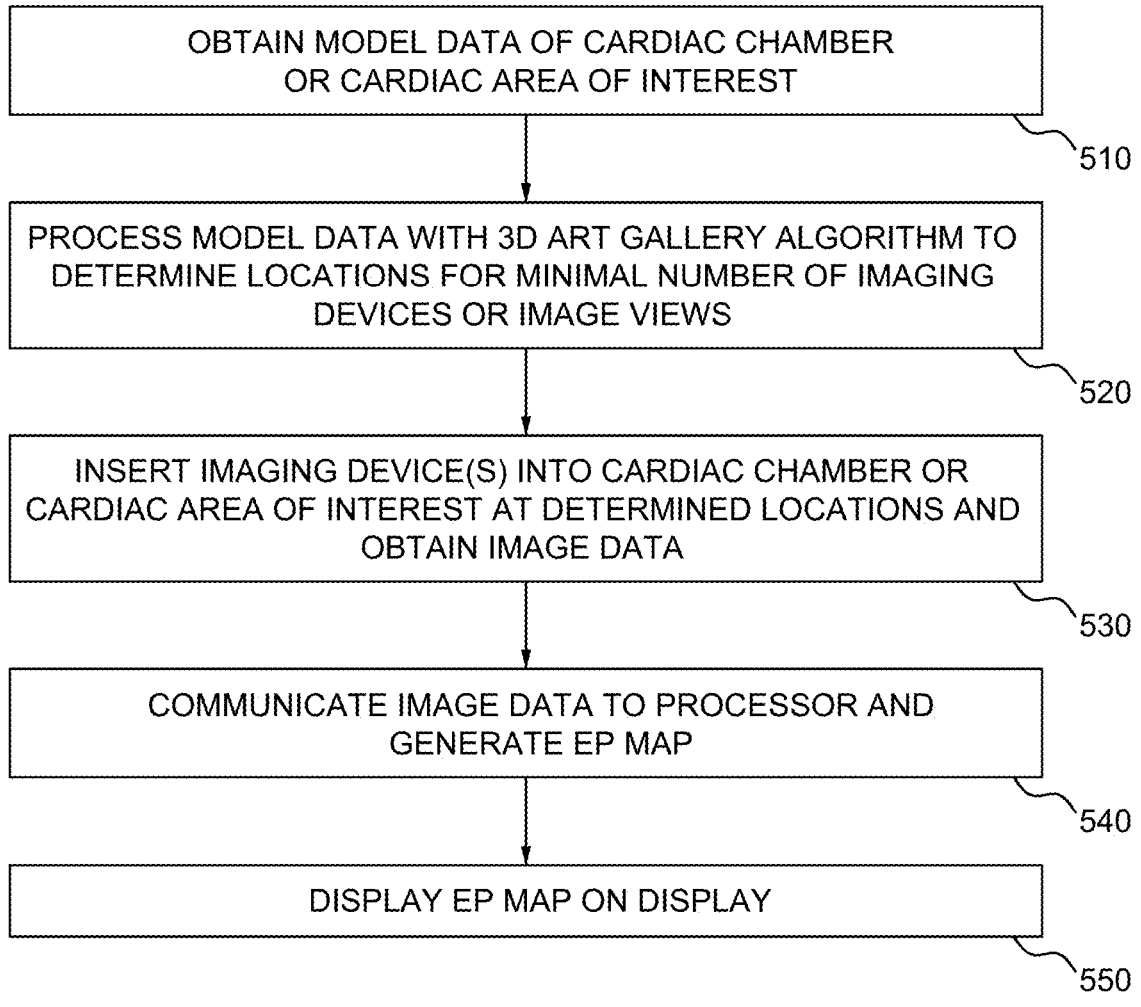

OBTAIN MODEL DATA OF CARDIAC CHAMBER OR CARDIAC AREA OF INTEREST

510

PROCESS MODEL DATA WITH 3D ART GALLERY ALGORITHM TO DETERMINE LOCATIONS FOR MINIMAL NUMBER OF IMAGING DEVICES OR IMAGE VIEWS

520

INSERT IMAGING DEVICE(S) INTO CARDIAC CHAMBER OR CARDIAC AREA OF INTEREST AT DETERMINED LOCATIONS AND OBTAIN IMAGE DATA

530

COMMUNICATE IMAGE DATA TO PROCESSOR AND GENERATE EP MAP

540

DISPLAY EP MAP ON DISPLAY

SYSTEMS AND METHODS FOR CARDIAC CHAMBER VISUALIZATION

FIELD OF INVENTION

The present invention is related to systems, methods, apparatuses, and programs for improved cardiac chamber visualization.

BACKGROUND

Visualization of cardiac structures is critical for observing and diagnosing cardiac health and to perform certain cardiac procedures. For example, cardiac arrhythmias such as atrial or ventricular fibrillation, ventricular tachycardia, and atrial flutter are a potentially significant cause of morbidity and death. Treatments for such cardiac conditions often require obtaining a detailed mapping of cardiac tissue, chambers, veins, arteries and/or electrical pathways to assist with identifying problem areas such as scar tissue, arrhythmia sources (e.g., electric rotors), healthy areas, and the like. As a prerequisite to performing a cardiac procedure, such as catheter ablation, the cause of the cardiac arrhythmia must be accurately located in the heart chamber. Such locating may be done via an electrophysiological investigation to generate an electrophysiological (EP) cardiac map in which 3D mapping data can be displayed on a monitor.

It is currently cumbersome to view ablation targets or sites in current EP cardiac maps. Current EP cardiac maps are viewed from outside the heart chamber or cardiac area of interest and require cumbersome steps of rotating and zooming the EP map to see ablation sites, such as in pulmonary veins, from multiple views.

It would be advantageous to a physician, such as cardiologist, to be able to view potential sites for ablation in a single view without having to rotate and zoom the EP cardiac map. In addition, it would be advantageous to a physician to view an EP cardiac map from inside a heart chamber in order to provide a more complete visualization of cardiac sites targeted for ablation, such as within a pulmonary vein, in a single view.

SUMMARY OF DISCLOSURE

Systems, methods, apparatuses, and programs for improved cardiac chamber visualization are disclosed herein.

In accordance with one an aspect, the subject matter disclosed herein relates to a system for visualizing a cardiac structure of interest. The system comprises at least one imaging device that obtains image data of the cardiac structure of interest from within the cardiac structure and a processor comprising a memory. The processor is configured to receive and store model data of the cardiac structure of interest, determine at least one location for positioning the at least one imaging device within the cardiac structure of interest to obtain image data of the cardiac structure of interest, receive the image data from the at least one imaging device positioned at the at least one determined location within the cardiac structure of interest, and generate a 3D electrophysiological map of the cardiac structure of interest from within the electrophysiological map based on the received image data.

In accordance with another aspect, the subject matter disclosed herein relates to a method for visualizing a cardiac structure of interest. The method comprises obtaining model data of a cardiac structure of interest, determining at least one location for positioning at least one imaging device within the cardiac structure of interest to obtain image data of the cardiac structure of interest positioning the at least one imaging device at the at least one determined location within the cardiac structure of interest, generating image data of the cardiac structure of interest from the at least one determined location within the cardiac structure of interest, and generating a 3D electrophysiological map of the cardiac structure of interest from within the electrophysiological map based on the generated image data.

In accordance with yet another aspect, the subject matter disclosed herein relates to a non-transitory computer readable recording medium storing program instructions for visualizing a cardiac structure of interest by causing a computer to execute the steps of: obtaining model data of a cardiac structure of interest, determining at least one location for positioning at least one imaging device within the cardiac structure of interest to obtain image data of the cardiac structure of interest, positioning the at least one image device at the at least one determined location within the cardiac structure of interest, generating image data of the cardiac structure of interest from the at least one determined location within the cardiac structure of interest, and generating a 3D electrophysiological map of the cardiac structure of interest from within the electrophysiological map based on the generated image data.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 5 is a flow diagram illustrating an exemplary process for generating an EP map of a cardiac chamber or cardiac area of interest from within the EP map utilizing in accordance with a disclosed embodiment of the present application.

DETAILED DESCRIPTION

Figure 1:
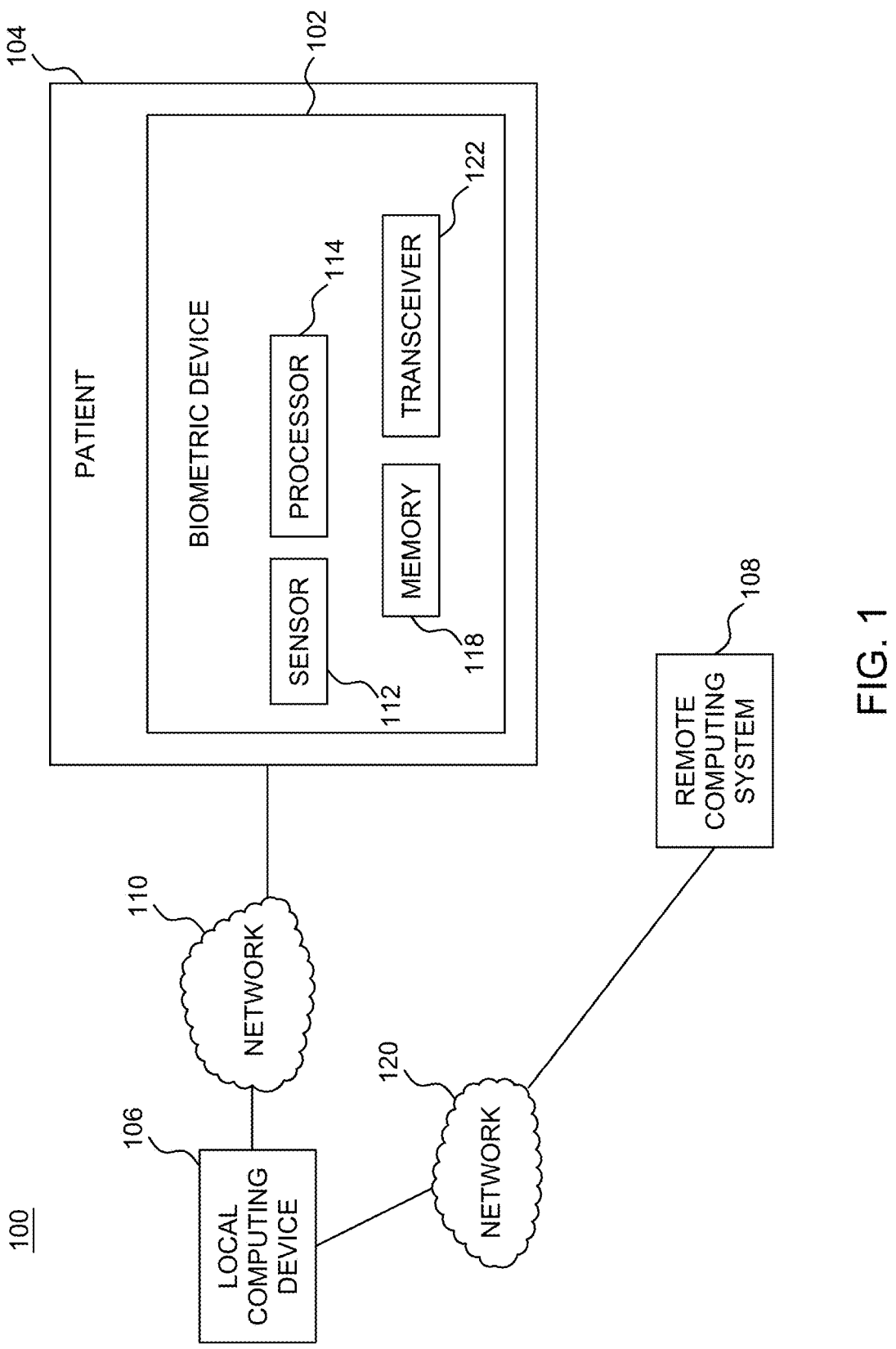
FIG. 1 is a block diagram depicting an exemplary computing environment of a system for improved cardiac visualization in accordance with disclosed embodiments of the present application.

Methods apparatuses, systems, and programs for improved cardiac chamber visualization are disclosed herein.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Patients with cardiac arrhythmias can be treated by catheter ablation.

A catheter ablation based treatment may include mapping the heart tissue, especially the endocardium, the heart volume, selective heart chambers, and pulmonary veins, and selectively ablating the cardiac tissue by application of energy. Cardiac mapping, for example, creating an electrophysiological (EP) map of electrical potentials (a voltage map) of the wave propagation along the heart tissue or a map of arrival times (a local time activation (LAT) map) to various tissue located points, may be used for detecting local heart tissue dysfunction. Ablations, such as those based on EP cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—EP mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) electrophysiological (EP) mapping systems in order to reconstruct the anatomy of the heart chamber of interest. For example, cardiologists rely upon the CARTO®3 3D mapping system, produced by Biosense Webster, Inc. (Diamond Bar, Calif.), to analyze cardiac tissue and determine the ablation points for treatment of a broad range of cardiac conditions. The 3D EP maps can provide multiple pieces of information regarding the electrophysiological properties of the cardiac tissue that represent the anatomical and functional substrate of these challenging arrhythmias.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having at least one electrode at its distal end, into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

In an embodiment, EP cardiac mapping may be implemented by sensing an electrical property of heart tissue, for example, local activation time (LAT), as a function of the precise location within the heart. The corresponding data may be acquired with one or more catheters that are advanced into the heart using catheters that have electrical and location sensors in their distal tips. As an example, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

FIG. 1 is a block diagram depicting a computing environment of an example system 100 for improved cardiac visualization in accordance with the subject matter of this application. In the example illustrated in FIG. 1, the system 100 includes a biometric device 102 associated with a patient 104, a local computing device 106, and optionally, a remote computing system 108, a first network 110, and a second network 120. In an embodiment, system 100 can be used with an EP mapping system.

According to an embodiment, the monitoring and processing apparatus 102 may be an apparatus that is internal to the patient's body (e.g., subcutaneously implantable). The biometric device 102 may be inserted into a patient via any applicable manner including surgical insertion via a vein or artery, an endoscopic procedure, or a laparoscopic procedure. According to an embodiment, the biometric device 102 may also include a catheter with one or more electrodes or a probe, or an imaging device. According to an embodiment, a biometric device 102 may include both components that are internal to the patient and components that are external to the patient.

A single biometric device 102 is shown in FIG. 1. However, one or more monitoring and processing apparatuses 102 may be used to acquire patient biometric data (e.g., electrical signals, image data, or other biometric data) and receive at least a portion of the patient biometric data representing the acquired patient biometrics. Each biometric device 102 may process data, including its own acquired patient biometrics as well as data received from one or more other monitoring and processing apparatuses 102.

In FIG. 1, network 110 is an example of a short-range network (e.g., local area network (LAN), or personal area network (PAN)). Information may be sent, via short-range network 110, between monitoring an processing apparatus 102 and local computing device 106 using any one of various short-range wireless communication protocols, such as Bluetooth, Wi-Fi, Zigbee, Z-Wave, near field communications (NFC), ultraband, Zigbee, or infrared (IR).

Network 120 may be a wired network, a wireless network or include one or more wired and wireless networks. For example, a network 120 may be a long-range network (e.g., wide area network (WAN), the internet, or a cellular network). Information may be sent, via network 120 using any one of various long-range wireless communication protocols (e.g., TCP/IP, HTTP, 3G, 4G/LTE, or 5G/New Radio).

The patient biometric device 102 may include a patient biometric sensor 112, a processor 114, a memory 118, and a transmitter-receiver (i.e., transceiver) 122. The patient biometric device 102 may continually or periodically monitor, store, process and communicate, via network 110, any number of various patient biometrics. Examples of patient biometrics include, without limitation, electrical signals and image signals. The patient biometrics may be monitored and communicated for treatment across any number of various diseases, such as cardiovascular diseases (e.g., arrhythmias, cardiomyopathy, and coronary artery disease).

Patient biometric sensor 112 may include, for example, one or more sensors configured to sense a type of biometric patient biometrics. For example, patient biometric sensor 112 may include an electrode configured to acquire electrical signals (e.g., cardiac signals) or images signals.

Transceiver 122 may include a separate transmitter and receiver. Alternatively, transceiver 122 may include a transmitter and receiver integrated into a single device.

Processor 114 may be configured to store patient data, such as patient biometric data in memory 118 acquired by patient biometric sensor 112, and communicate the patient data, across network 110, via a transmitter of transceiver 122. Data from one or more other biometric device 102 may also be received by a receiver of transceiver 122.

The local computing device 106 of system 100 is in communication with the patient biometric device 102 and may be configured to act as a gateway to the remote computing system 108 through the second network 120. The local computing device 106 may be, for example, a, smart phone, smartwatch, tablet or other portable smart device configured to communicate with other devices via network 120. Alternatively, the local computing device 106 may be a stationary or standalone device, such as a stationary base station including, for example, modem and/or router capability, a desktop or laptop computer using an executable program to communicate information between the processing apparatus 102 and the remote computing system 108 via the PC's radio module, or a USB dongle. Patient biometrics may be communicated between the local computing device 106 and the patient biometric device 102 using a short-range wireless technology standard (e.g., Bluetooth, Wi-Fi, Zig-Bee, Z-wave and other short-range wireless standards) via the short-range wireless network 110, such as a local area network (LAN) (e.g., a personal area network (PAN)). In some embodiments, the local computing device 106 may also be configured to display the acquired patient electrical signals and information associated with the acquired patient electrical signals, as described in more detail below.

In some embodiments, remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, such as any of the wireless technologies mentioned above. As described in more detail below, the remote computing system 108 may be configured to provide (e.g., visually display and/or aurally provide) the at least one of the patient biometrics and the associated information to a healthcare professional (e.g., a physician).

In an embodiment, the remote computing system 108 can be incorporated in a public cloud computing platform (such as Amazon Web Services or Microsoft Azure), a hybrid cloud computing platform (such as HP Enterprise One-Sphere) or a private cloud computing platform. In an embodiment, the remote computing system 108 may include one or more processors that perform various functions such as, without limitation, analyzing monitored patient biometrics and, according to physician-determined or algorithm driven thresholds and parameters, providing alerts, additional information or instructions. The remote computing system 108 may be used to provide healthcare personnel with a dashboard of patient information, such that such information may enable healthcare personnel to identify and prioritize patients having more critical needs than others.

Figure 2:
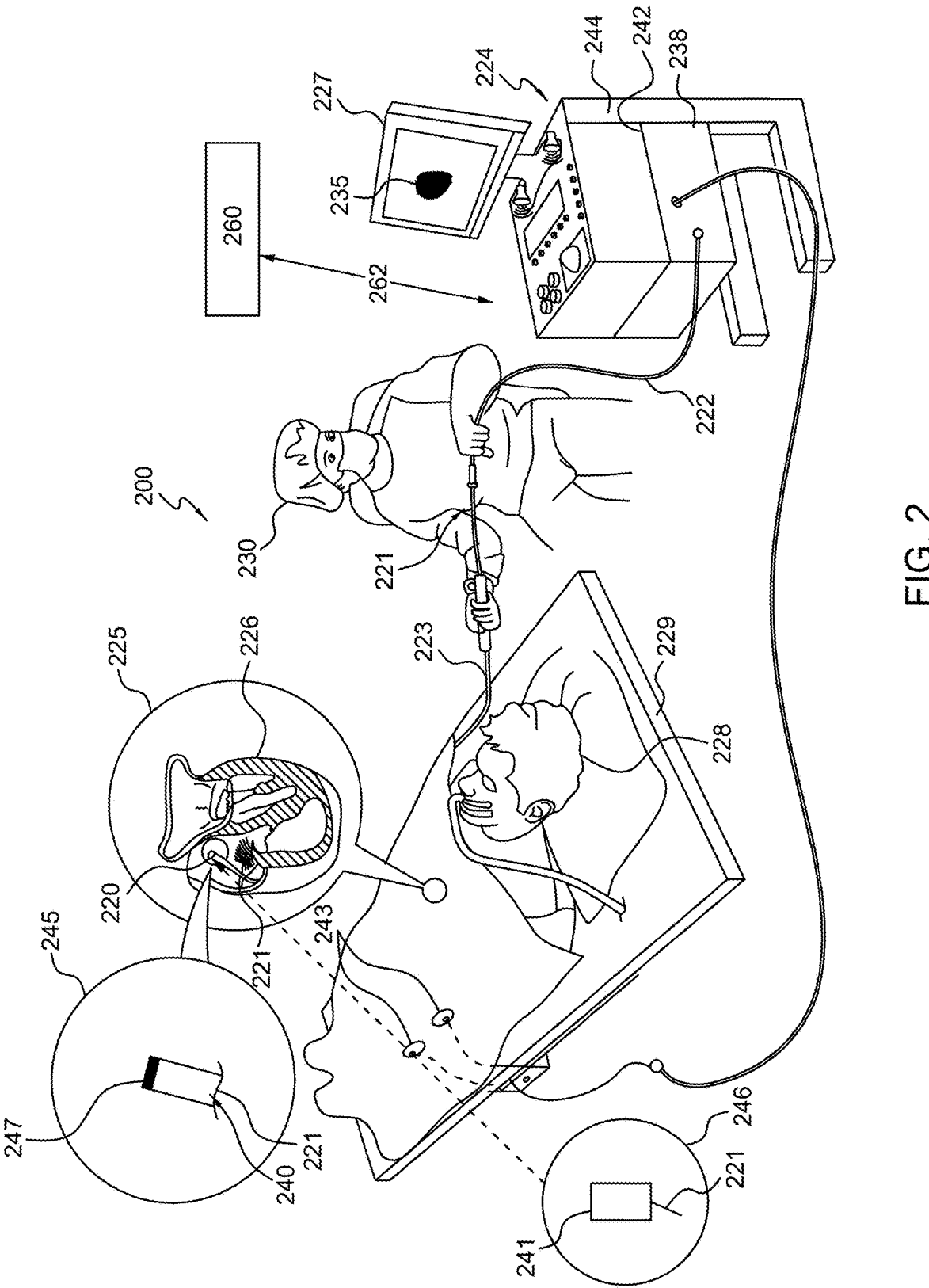
FIG. 2 shows an exemplary electrophysiological (EP) mapping system in which one or more features of the disclosed subject matter can be implemented in accordance with disclosed embodiments of the present application.

FIG. 2 is a diagram of an exemplary EP mapping system 200 in which one or more features of the disclosed subject matter can be implemented. EP mapping system 200 may include one or more biometric devices 220 (illustrated in inset 225), such as a catheter 240 (illustrated in inset 245), or an imaging device 241, such as an image sensor or a camera (illustrated in inset 246). Alternatively, the biometric device 220 can be a catheter that includes an imaging device, and optionally, an ablation device and an illumination device. Biometric device 220 can be the biometric device 120 depicted in FIG. 1. The biometric devices 220 may be configured to obtain biometric data, such as imaging signals or electronic signals. One of skill in the art will recognize that catheter 240 and imaging device 241 can be any shape and can includes one or more elements (e.g., electrodes or sensors) used to implement the embodiments disclosed herein. EP mapping system 200 includes a probe 221, having one or more shafts 222 that may be navigated by a physician 230 into a body part, such as heart 226, of a patient 228 lying on a table 229. According to embodiments, multiple probes 221 may be provided, however, for purposes of conciseness, a single probe 221 is described in this example, but it will be understood that probe 221 may represent multiple probes. As shown in FIG. 2, physician 230 may insert probe 221 through a sheath 223, while manipulating shaft 222 at the distal end of probe 221 using a manipulator near the proximal end of the invasive device and/or deflection from the sheath 223. As shown in an inset 225, a biometric device 220 may be fitted at the distal end of probe 221. Biometric device 220 may be inserted through sheath 223 to obtain biometric data of heart 226. For example, catheter 240 may include at least one ablation electrode 247 and a catheter needle.

According to an embodiment, catheter 240 may be configured to ablate tissue areas of a cardiac chamber of heart 226. Inset 245 shows catheter 240 in an enlarged view, inside a cardiac chamber of heart 226. As shown, catheter 240 may include at least one ablation electrode 247 coupled onto the body of the catheter. According to other embodiments, multiple elements may be connected via splines that form the shape of the catheter 240. One or more other elements (not shown) may be provided and may be any elements configured to ablate or to obtain biometric data and may be electrodes, transducers, or one or more other elements.

According to another embodiment, imaging device 241 may be configured to obtain image data, for example, such as image data 235, from outside of the heart 226 or within a cardiac chamber. Inset 246 shows imaging device 241 in an enlarged view, inside a cardiac chamber of heart 226. One of skill in the art will recognize that multiple imaging devices 241 can be utilized to obtain images of the heart 226 from multiple positions or angles. One of skill in the art will recognize that imaging device 241 may be any camera or image sensor that can convert an optical image into an electronic signal. In some embodiments, the imaging device can be a miniature CMOS image sensor with a lens or a CCD camera or other image sensor that can convert an optical image into an electronic signal.

According to embodiments disclosed herein, biometric data may also include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 2, the probe 221 may be connected to a console 224. Console 224 may include a processor 244, such as a general-purpose computer, with suitable front end and interface circuits 238 for transmitting and receiving signals to and from biometric device 220, as well as for controlling the other components of EP mapping system 200. In some embodiments, processor 244 may be further configured to receive biometric data, such as electrical activity, and determine if a given tissue area conducts electricity. According to an embodiment, the processor may be external to the console 224 and may be located, for example, in the catheter, in an external device, in a mobile device, in a cloud-based device, or may be a standalone processor.

As noted above, processor 244 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 2 may be modified to implement the embodiments disclosed herein. The disclosed embodiments may similarly be applied using other system components and settings. Additionally, EP mapping system 200 may include additional components, such as elements for sensing electrical activity, wired or wireless connectors, processing and display devices, or the like.

According to an embodiment, a display 227 connected to a processor (e.g., processor 244) may be located at a remote location such as a separate hospital or in separate healthcare provider networks. Additionally, the EP mapping system 200 may be part of a surgical system that is configured to obtain anatomical and electrical measurements of a patient's organ, such as a heart, and performing a cardiac ablation procedure. An example of such a surgical system is the Carto® system sold by Biosense Webster.

The EP mapping system 200 may also, and optionally, obtain biometric data such as anatomical measurements of the patient's heart using ultrasound, computed tomography (CT), magnetic resonance imaging (MRI) or other medical imaging techniques known in the art. The EP mapping system 200 may obtain electrical measurements using catheters 240, imaging devices 241, body surface electrodes 243 or other sensors that measure electrical properties of the heart. The biometric data including anatomical and electrical measurements may then be stored in a memory 242 of the EP mapping system 200, as shown in FIG. 2. The biometric data may be transmitted to the processor 244 from the memory 242. Alternatively, or in addition, the biometric data may be transmitted to a server 260, which may be local or remote, using a network 262.

Network 262 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the EP mapping system 200 and the server 260. The network 262 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 262.

In some instances, the server 260 may be implemented as a physical server. In other instances, server 262 may be implemented as a virtual server a public cloud computing provider (e.g., Amazon Web Services (AWS)®).

Processor 244 may include real-time noise reduction circuitry typically configured as a field programmable gate array (FPGA), followed by an analog-to-digital (A/D) ECG (electrocardiograph) or EMG (electromyogram) signal conversion integrated circuit. The processor 244 may pass the signal from an A/D ECG or EMG circuit to another processor and/or can be programmed to perform one or more functions disclosed herein.

Control console 224 may also include an input/output (I/O) communications interface that enables the control console to transfer signals from, and/or transfer signals to biometric device 220.

During a procedure, processor 244 may facilitate the presentation of a body part rendering to physician 230 on a display 227, and store data representing the body part rendering 235 in a memory 242. Memory 242 may comprise any suitable volatile and/or non-volatile memory, such as random-access memory or a hard disk drive. In some embodiments, medical professional 230 may be able to manipulate a body part rendering 235 using one or more input devices such as a touch pad, a mouse, a keyboard, a gesture recognition apparatus, or the like. For example, an input device may be used to change the position of catheter 240 such that rendering 235 is updated. In alternative embodiments, display 227 may include a touchscreen that can be configured to accept inputs from medical professional 230, in addition to presenting a body part rendering 235.

Figure 3A:
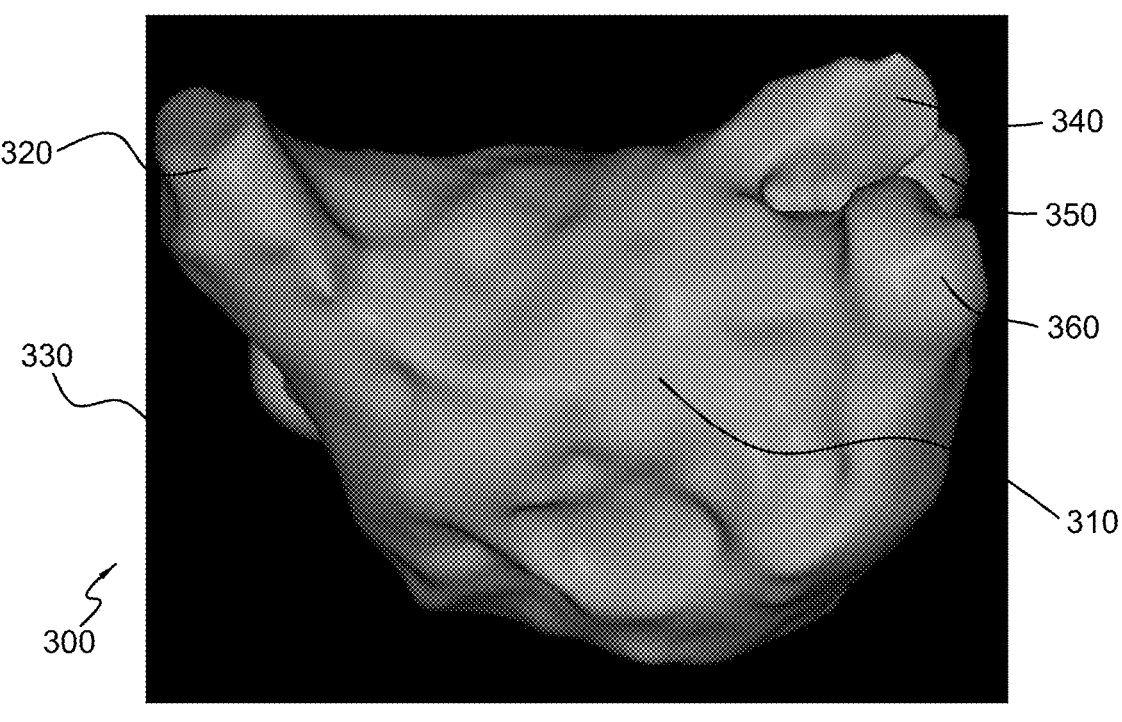
FIGS. 3A and 3B illustrate conventional views of an EP map of a left atrium showing pulmonary veins observed from outside of the heart chamber or outside of the EP map.
Figure 3B:
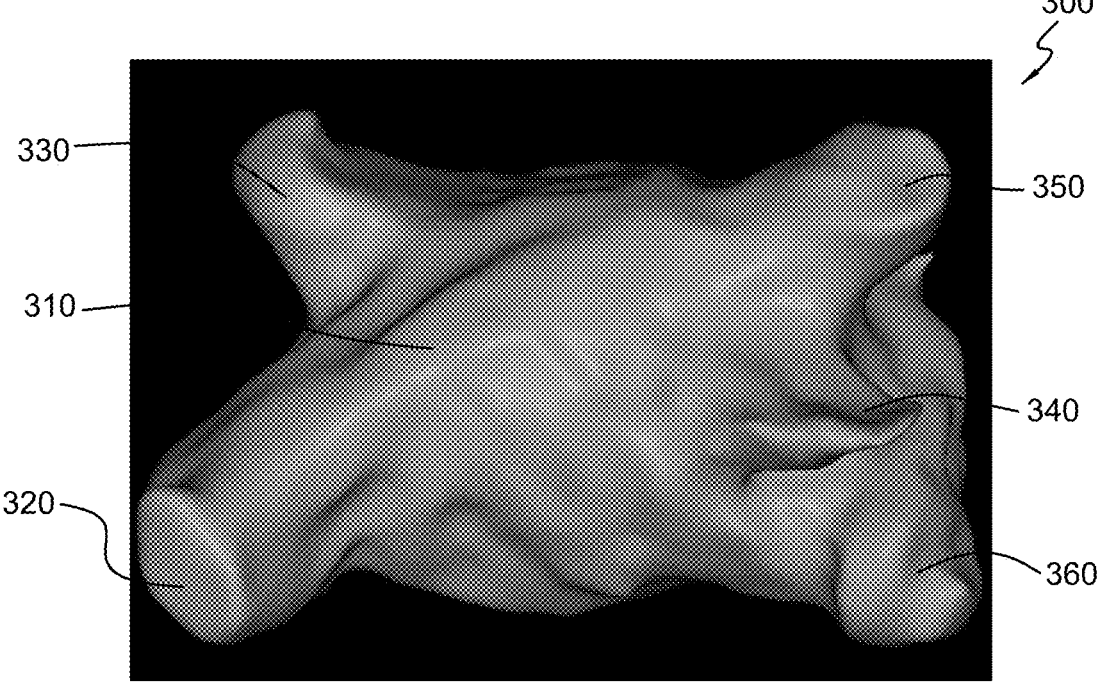

Current EP mapping systems generate EP maps of the heart that are viewed from outside a heart chamber and require cumbersome steps of rotating and zooming the map to see ablation sites, such as in pulmonary veins, from multiple views. For example, FIGS. 3A and 3B illustrate conventional views of an EP map 300 of a left atrium 310 of the heart showing the pulmonary veins observed from outside of the heart chamber or outside of the EP map 300. More particularly, FIGS. 3A and 3B illustrates the right superior pulmonary vein (RSPV) 320, right inferior pulmonary vein (RIPV) 330, left superior pulmonary vein (LSPV) 340, left inferior pulmonary vein (LIPV) 350, and left atrial appendage (LAA) 360 observed from outside of the left atrium 310.

Conventional EP maps illustrating a heart chamber have several drawbacks. For example, the visualization can simulate an orthographic camera in which elements having different depths appear the same. This makes it difficult to decide how close a catheter, such as an ablation catheter, is to the EP map surface. For example, the catheter can be closer to the front surface or the back surface of the EP map and will visually appear the same. Conventional EP mapping systems attempt to compensate for this visual ambiguity by providing a catheter distance projection to assist understanding the depth of the catheter.

Another drawback with conventional EP maps is that the veins can obscure each other. For example, as shown in FIG. 3A, portions of the RIPV 330 are obstructed by the RSPV 320 and portions of the LIPV 350 are obstructed by the LSPV 340. In order to view the various veins in such conventional EP mapping systems, the map 300 must be rotated in order to see the obscured portions.

Figure 4:
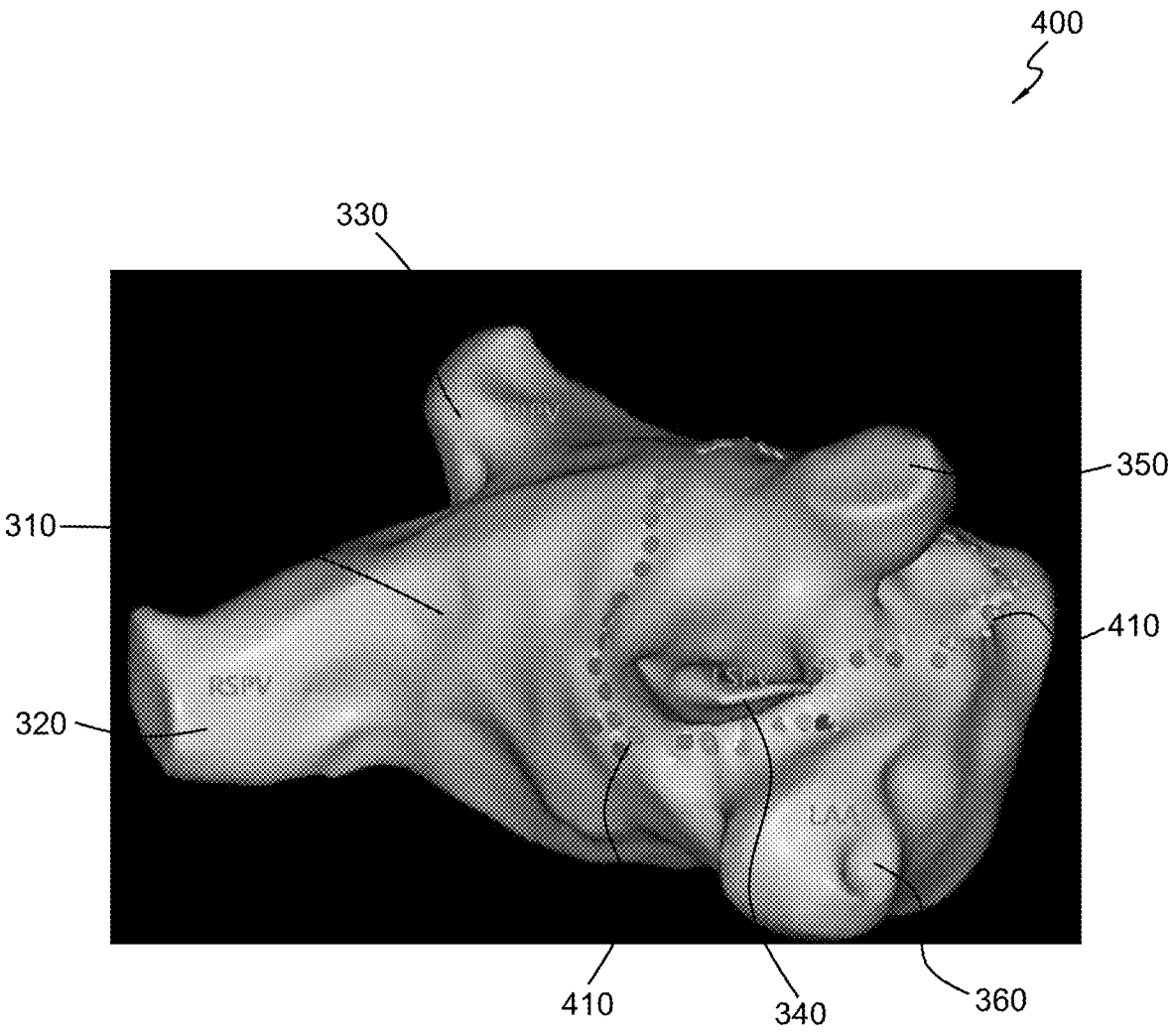
FIG. 4 illustrates a conventional view of an EP map of a left atrium showing locations identified for ablation.

Yet another drawback with conventional EP maps is that the map is viewed from outside the cardiac chamber while the catheter is inside the chamber, causing the position of the catheter relative to the veins to be unclear. In addition, during an ablation procedure, the area identified for ablation around a vein cannot be viewed in a single view. For example, FIG. 4 illustrates a view of an EP map 400 of the left atrium 310 of the heart showing locations 410 identified for ablation around the LSPV 340 and LIPV 350 viewed from outside of the heart chamber or outside of the EP map. As illustrated in FIG. 4, all of the locations 410 identified for ablation cannot be observed in a single view, and requires rotation of the EP map 400 to view the obscured locations 410 for ablation.

In an embodiment, the subject matter of the present application is directed to utilizing positioning algorithms to determine locations within a cardiac structure to position one or more imaging devices, such as imaging device 241 (FIG. 2), or to obtain image views of the cardiac chamber to generate a 3D EP map of the entire chamber or cardiac area of interest from within the cardiac chamber or cardiac area of interest, without the need for a physician to rotate and zoom the EP map to view the entire chamber or cardiac area of interest. In an embodiment, the subject matter of the present application utilizes an imaging device, such as a perspective camera, to provide improved 3D depth for the EP map as compared to conventional orthogonal camera views.

In an embodiment, the subject matter of the present application can be used to generate a view of an entire cardiac chamber from inside the chamber or EP map. In yet another embodiment, the subject matter of the present application can be used to generate a view of a cardiac area of interest, such as, without limitation, a pulmonary vein, appendage, vein bifurcation, etc. In yet another embodiment, the subject matter of the present application can be used during a cardiac procedure, such as, without limitation, an ablation procedure to view locations identified for ablation from within the EP map in a single view.

In an embodiment, the subject matter of the present application is directed to a system, such as EP mapping system 200, or method for visualizing a cardiac structure of interest. The system preferably comprises at least one imaging device, for example, imaging device 241, that obtains image data, for example, image data 235, of the cardiac structure of interest from within the cardiac structure and a processor, for example, processor 244, comprising a memory, for example, memory 242. The processor is configured to receive and store model data of the cardiac structure of interest, determine at least one location for positioning the at least one imaging device within the cardiac structure of interest to obtain image data of the cardiac structure of interest, receive the image data from the at least one imaging device positioned at the at least one determined location within the cardiac structure of interest, and generate a 3D electrophysiological map of the cardiac structure of interest from within the electrophysiological map based on the received image data.

3D Art Gallery Algorithm

In an embodiment, the subject matter of the present application utilizes the "art gallery problem" to identify optimal areas for placement of an imaging device, such as imaging device 241, within a cardiac chamber to generate a three-dimensional (3D) view of the entire cardiac chamber or cardiac area of interest from within the chamber or EP map.

The "art gallery problem" is a well-known problem in the field of computational geometry and is readily understood by one of skill in the art. For example, the "art-gallery problem" conventionally involves placing minimal number of guards (i.e., cameras) in a two-dimensional (2D) closed polygon art gallery, such that the guards are able to view the entire area of the polygon. In other words, all locations within the gallery are able to be viewed by at least one guard. In the field of computational geometry, algorithms are utilized to solve the problem. For example, given a simple polygon having n vertices, the minimum number of guards to see every point within the interior of the polygon is (n/3) guards.

Two-dimensional (2D) and three-dimensional (3D) "art gallery problems" and algorithms for solving 2D and 3D art gallery problems are well known and described in the art and described. See, for example, O'Rourke, Joseph, "Art Gallery Theorems And Algorithms," New York, Oxford University Press, Inc. (1987), Csizmadia et al., "Note On Art Gallery Problem," Computational Geometry, Vol. 10, p. 47-55 (1998), and Marzal, Jefri, "The Three-Dimensional Art Gallery Problem And Its Solutions," Murdoch University School of Information Technology (2012), the contents of which are incorporated herein by reference as if fully set forth. In an embodiment, the subject matter of the present application utilizes the 3D art gallery problem to determine locations for the minimum number of imaging devices, such as imaging device 241, to be positioned within a cardiac chamber to generate a 3D view of the entire chamber or cardiac area of interest. According to the subject matter of the present application, any known algorithm or approximation algorithm described in the literature for solving the 3D art gallery problem can be utilized.

In an embodiment, a 3D art gallery algorithm is utilized to determine the locations for the minimal number of imaging devices or imaging views from within the EP map to create a complete visualization of the cardiac chamber or cardiac location of interest. The images obtained from the minimum number of imaging device locations or views creates are combined to generate an EP map with a single view of the entire cardiac chamber or cardiac area of interest, so that the physician is not required to rotate and zoom the EP map to view the entire cardiac chamber or ablation site.

In accordance with an embodiment, the present application utilizes imaging devices, such as imaging device 241 used with EP mapping system 200 as described above with respect to FIG. 2, to generate views of an interior of a cardiac chamber or cardiac area of interest. As discussed above, one or more imaging devices 241 can be positioned within a cardiac chamber via probe 221 or shaft 222. The imaging devices 241 are used to obtain image data of the cardiac chamber or cardiac area of interest and can be in communication with a processor or computing device, such as processor 114 and computing devices 106 and 108 as described with reference to FIG. 1, or processor 244 and server 260 as described with reference to FIG. 2, to generate an EP map with a view of the cardiac chamber or cardiac area of interest from inside the cardiac chamber or EP map.

FIG. 5 is an exemplary embodiment of a method or process 500 for generating an EP map of a cardiac chamber or cardiac area of interest from within the EP map utilizing the 3D gallery algorithm described herein.

At step 510, a processing device, such as processor 244 and memory, such as memory 242, associated with EP mapping system 200 (FIG. 2), preferably receives and stores model data associated with a cardiac chamber or cardiac area of interest. The model data can be obtained by an imaging system, such as, without limitation, by magnetic resonance imaging (MRI), computed tomography (CT) scan, x-ray imaging, rotational angiography, ultrasound imaging, three-dimensional ultrasound imaging, three-dimensional mapping, an intracardiac probe having an imaging device, or any other means for three-dimensional imaging. The model data can be obtained in real-time, from a previously generated model data of a patient's heart, or from a database of cardiac model data.

At step 520, the processing device preferably processes the model data associated with the cardiac chamber or cardiac area of interest utilizing the 3D art gallery algorithm described above to determine the locations within the cardiac chamber or cardiac area of interest to position the minimal number of imaging devices or to obtain the minimum number of image views to generate an EP map with a complete visualization of the cardiac chamber or cardiac location of interest from within the EP map. For example, and without limitation, the 3D art gallery algorithm utilized herein can be "The Fixed-Point Guard Placement Algorithm" described in Marzal, Jefri, "The Three-Dimensional Art Gallery Problem And Its Solutions," Murdoch University School of Information Technology (2012), which is incorporated by reference as if fully set forth.

At step 530, at least one probe comprising at least one imaging device, such as probe 221 and imaging device 241 described above with respect to FIG. 2, is preferably inserted into a cardiac chamber or cardiac area of interest at the determined locations and obtains image data of the cardiac chamber or cardiac location of interest at the determined locations. For example, and without limitation, the imaging device can have a positioning sensor to assist with locating the imaging device at the determined location.

Alternatively, at step 520 the processing device can utilize the 3D art gallery algorithm to suggest locations within the cardiac chamber or cardiac area of interest to position an image device or obtain image data, and a physician or technician can select the preferred locations to generate the EP map in step 530.

At step 540, the obtained image data is preferably communicated to the processing device, such as processor 244, to generate a 3D EP map of the cardiac chamber or cardiac area of interest from within the EP map with a complete visualization of the cardiac chamber or cardiac location of interest. The imaging device may transmit the image data to the processing device via a wired or wireless transmission means as described above.

At step 550, the generated 3D EP map can optionally be displayed on a display, such as display 227 (FIG. 2).

Figure 6A:
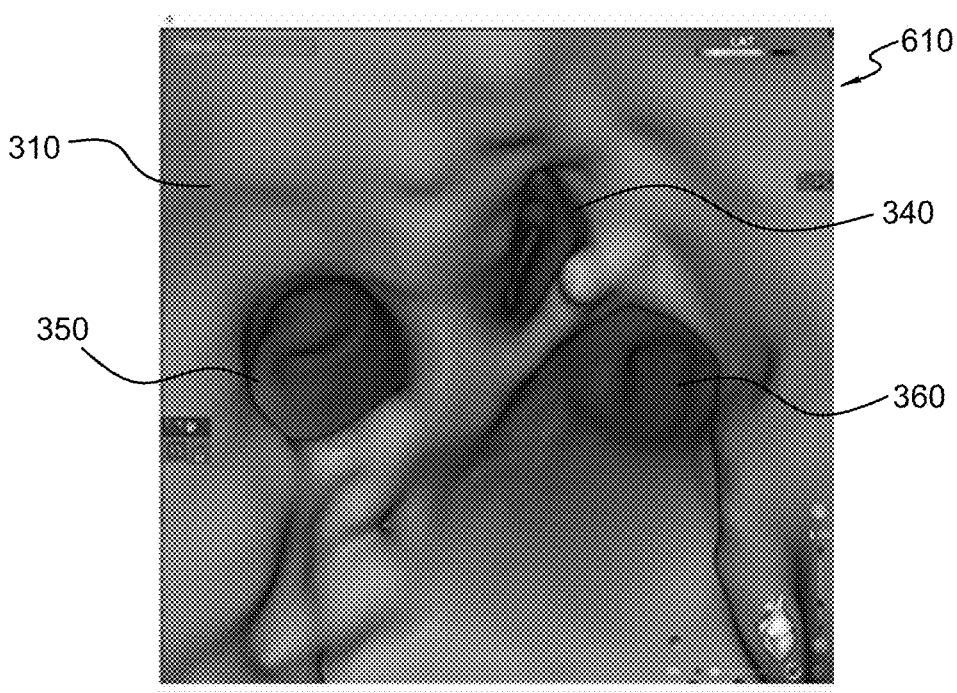
FIGS. 6A and 6B illustrate exemplary EP maps of a left atrium showing a complete visualization of the depicted pulmonary veins from inside the respective EP maps in accordance with a disclosed embodiment of the present application.
Figure 6B:
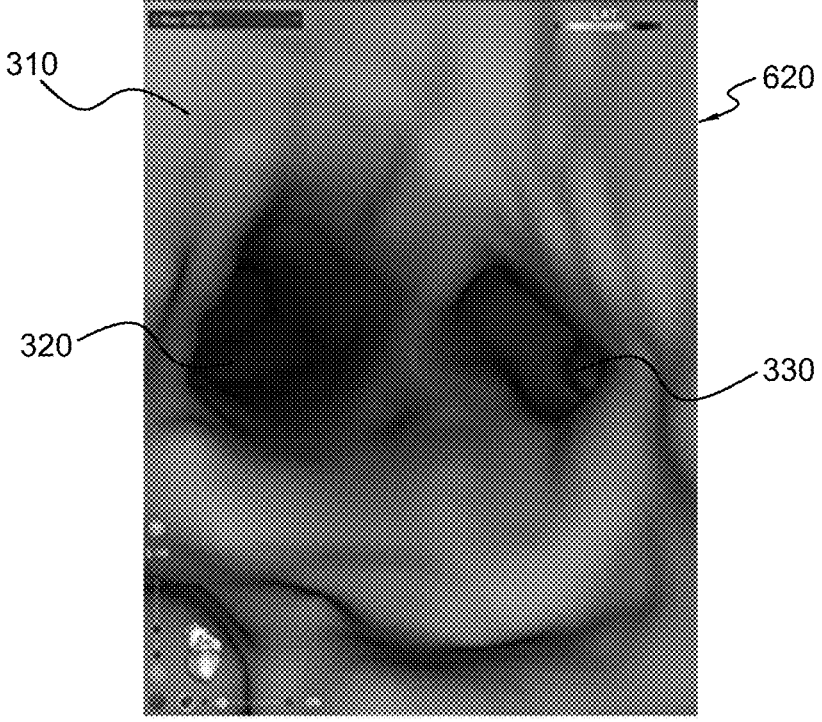
Figure 6C:
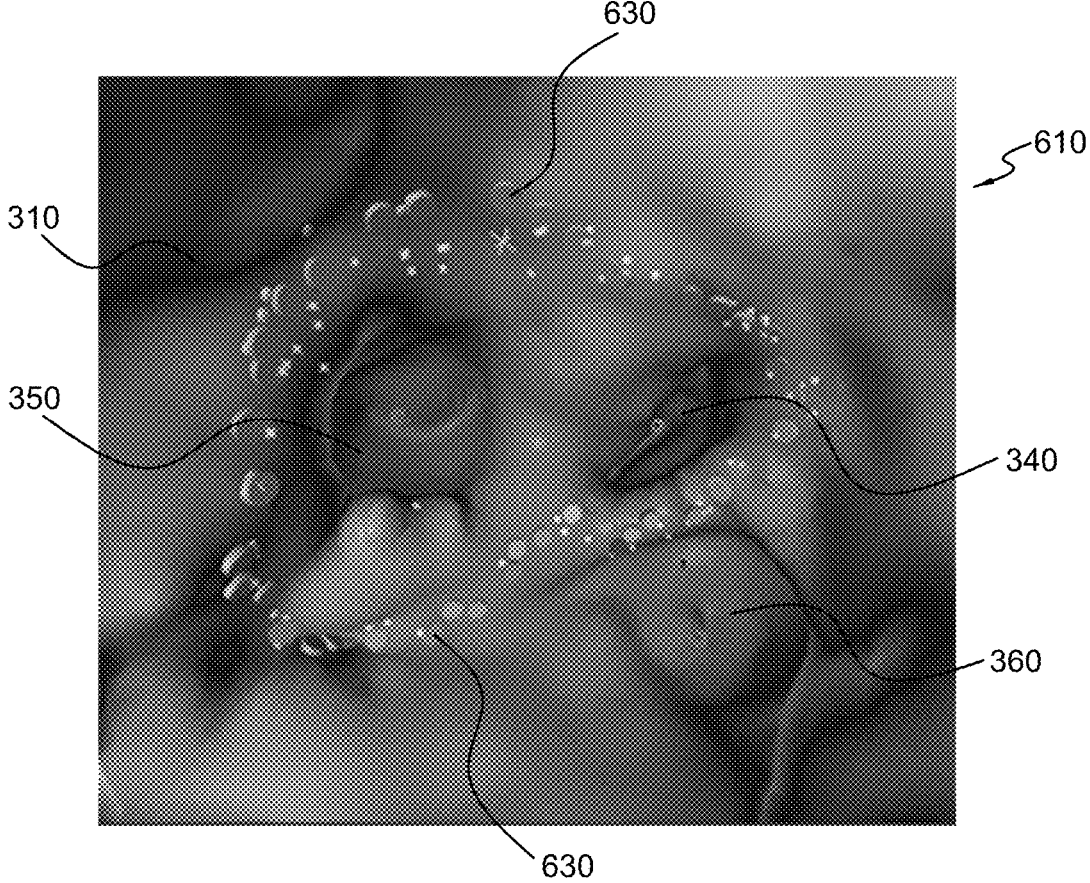
FIG. 6C illustrates the EP map of FIG. 6A showing a complete view of the locations identified for ablation around the depicted pulmonary veins viewed from inside the EP map in accordance with a disclosed embodiment of the present application.

FIGS. 6A, 6B, and 6C illustrate exemplary EP maps 610 and 620, respectively, of the left atrium 310 generated in accordance with process 500. FIG. 6A illustrates an exemplary view of the left atrium 310 showing a complete visualization of the LSPV 340, LIPV 350, and LAA 360 from inside the EP map 610. FIG. 6B illustrates an exemplary view of the left atrium 310 showing a complete visualization of the RSPV 320 and RIPV 330 from inside the EP map 620. FIG. 6C illustrates the EP map 610 of FIG. 6A showing a complete view of the locations 630 identified for ablation around the LSPV 340 and LIPV 350 viewed from inside the EP map 610. As shown in FIG. 6C, all of the locations 630 identified for ablation around the LSPV 340 and LIPV 350 can be viewed without the need to rotate the EP map 610. By comparison, the conventional EP map 400 of the outside of the heart chamber depicted in FIG. 4 and described above requires rotation of the map 400 to view all locations 410 identified for ablation around the LSPV 340 and LIPV 350.

Skeleton Axis Algorithm

In another embodiment, the subject matter of the present application utilizes a skeleton axis algorithm to generate a skeleton axis of a cardiac chamber or cardiac area of interest to identify optimal areas for placement of an imaging device, such as imaging device 241, within the cardiac chamber to generate a three-dimensional (3D) view of the cardiac area of interest from within the chamber or EP map.

Figure 7:
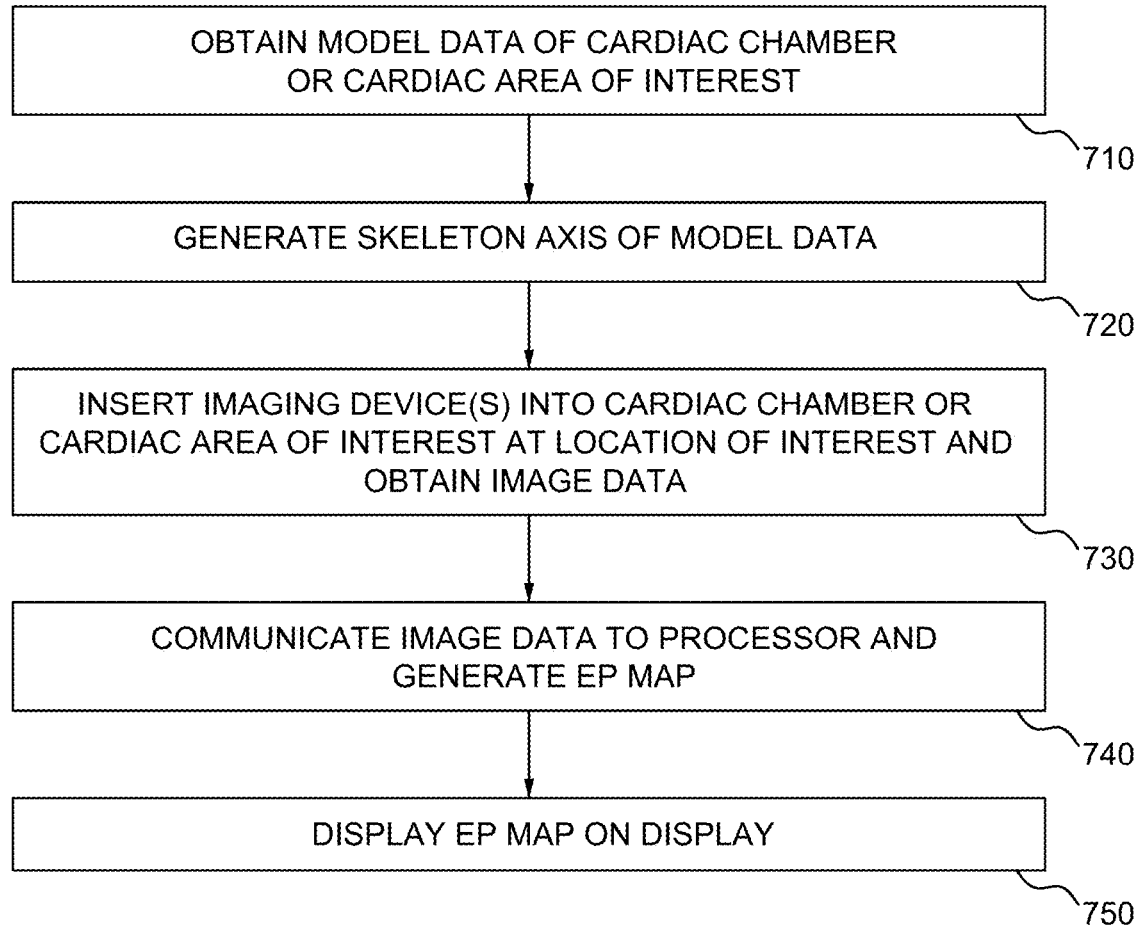
FIG. 7 is a flow diagram illustrating an exemplary process for generating an EP map of a cardiac chamber or cardiac area of interest from within the EP map in accordance with another disclosed embodiment of the present application.

FIG. 7 is an exemplary embodiment of a process 700 for generating an EP map of a cardiac area of interest from within the EP map utilizing a skeleton axis algorithm as described herein.

At step 710, a processing device, such as processor 244 and memory 242 associated with EP mapping system 200 (FIG. 2), preferably receives and stores model data associated with a cardiac chamber or cardiac area of interest. The model data can be obtained by an imaging system, such as, without limitation, by magnetic resonance imaging (MRI), computed tomography (CT) scan, x-ray imaging, rotational angiography, ultrasound imaging, three-dimensional ultrasound imaging, three-dimensional mapping, an intracardiac probe having an imaging device, or any other means for three-dimensional imaging. The model data can be obtained in real-time, from a previously generated model data of a patient's heart, or from a database of cardiac model data.

At step 720, the processing device preferably generates a skeleton axis or topographical skeleton of the cardiac chamber or cardiac area of interest by known methods and algorithms for creating a skeleton axis for triangulated meshes. An exemplary method for creating a skeleton axis involves generating a surface mesh in the 3D model data, such as a polygon mesh or triangular mesh, according to known methods for graphical modeling. The surface mesh is then collapsed to generate a medial axis or main axis along the medial portion of the structure and any extending branch portions, such as, without limitation, veins, arteries, appendages, etc. One of ordinary skill in the art will recognize that other methods or algorithms for generating a skeleton axis can be utilized within the scope of the present application, such as those described in Tagliasacchi et al., "Mean Curvature Skeletons," Computer Graphics Forum (Proceedings of the Symposium on Geometry Processing), 31(5):1735-1744 (2012), the contents of which is incorporated herein by reference.

Figure 8:
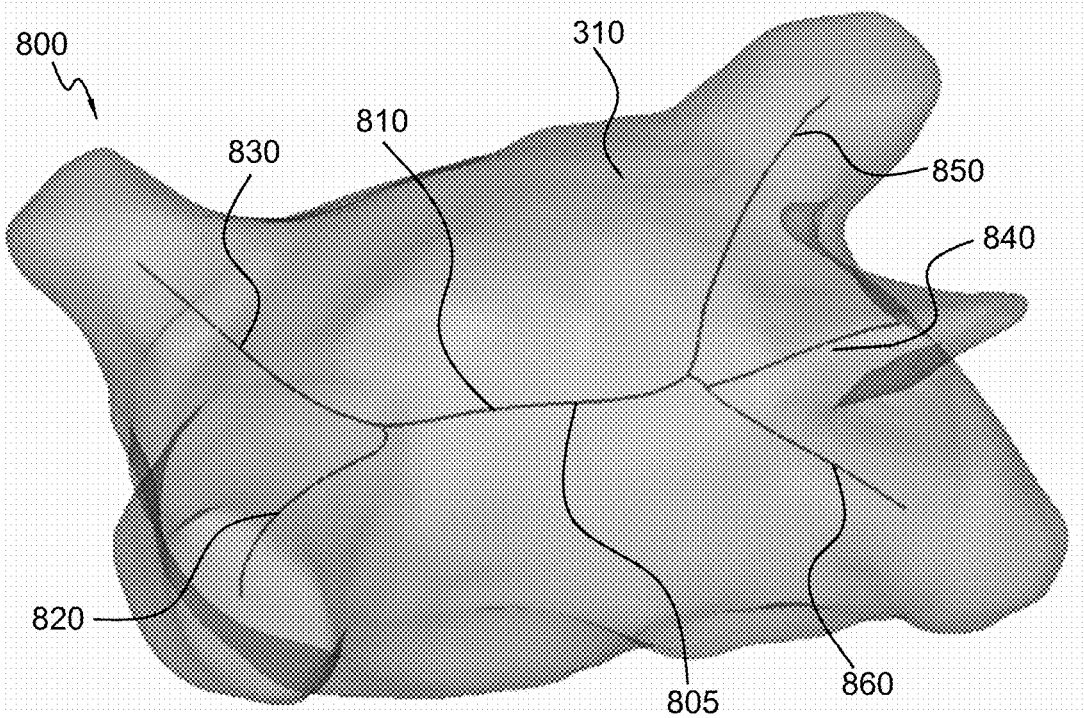
FIG. 8 illustrates an exemplary skeleton axis displayed on 3D model data of a left atrium 310 in accordance with a disclosed embodiment of the present application.

FIG. 8 illustrates an exemplary embodiment of a skeleton axis 805 displayed on the 3D model data 800 of the left atrium 310 in accordance with step 720 of FIG. 7. The skeleton axis 805 includes a main axis 810 and five (5) branch axes comprising: an RSPV axis 820, an RIPV axis 830, an LSPV axis 840, an LIPV axis 850, and an LAA 860 axis.

At step 730, at least one probe comprising at least one imaging device, such as probe 221 and imaging device 241 described above with respect to FIG. 2, is preferably inserted into a cardiac chamber or cardiac area of interest at a location of interest along the generated skeleton axis to obtain image data of the cardiac location of interest. For example, the location of interest can be along a vein or adjacent a vein bifurcation to view the entire area, and can be determined by a physician, such as a cardiologist.

Figure 9A:
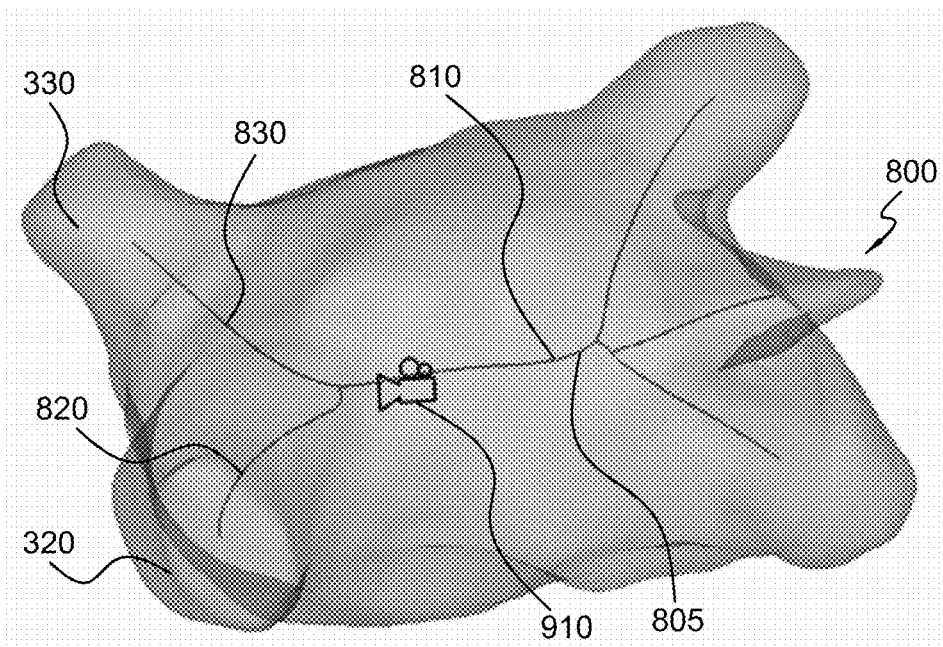
FIG. 9A illustrates an imaging device positioned within a left atrium to obtain a view of the right superior pulmonary vein (RSPV) and right inferior pulmonary vein (RIPV) from inside the cardiac chamber in accordance with a disclosed embodiment of the present application.
Figure 9B:
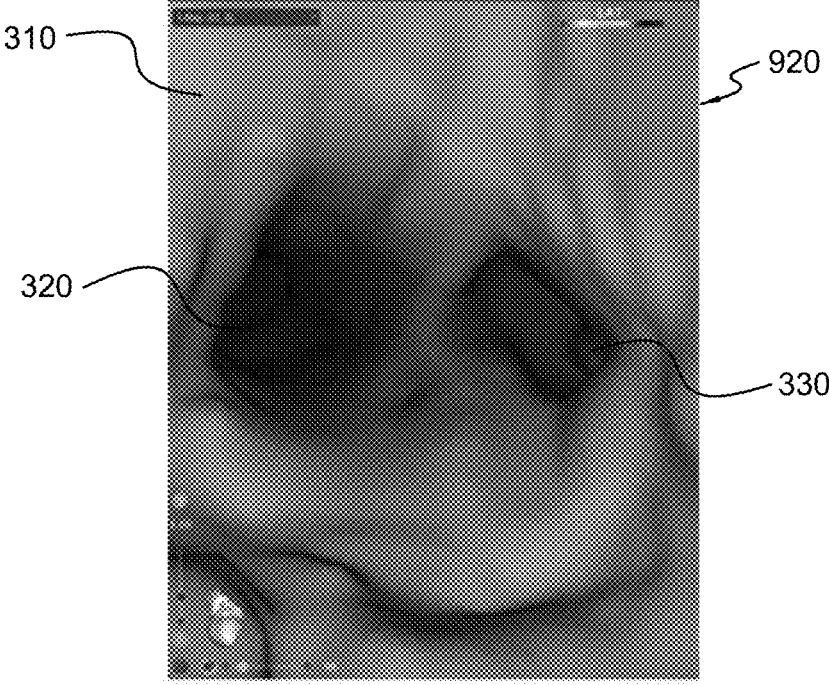
FIG. 9B illustrates an image of the RSPV and RIPV from inside the cardiac chamber obtained from the imaging device illustrated in FIG. 9A.

FIG. 9A illustrates an exemplary embodiment of an imaging device 910 positioned within a left atrium 310 along the main axis 810 of the skeleton axis 805 adjacent a bifurcation junction of the RSPV axis 820 and RIPV axis 830 to obtain a view of the RSPV 320 and RIPV 330 from inside the cardiac chamber. FIG. 9B illustrates an image of the RSPV 320 and RIPV 330 from inside the cardiac chamber obtained from imaging device 910 illustrated in FIG. 9A.

Figure 10A:
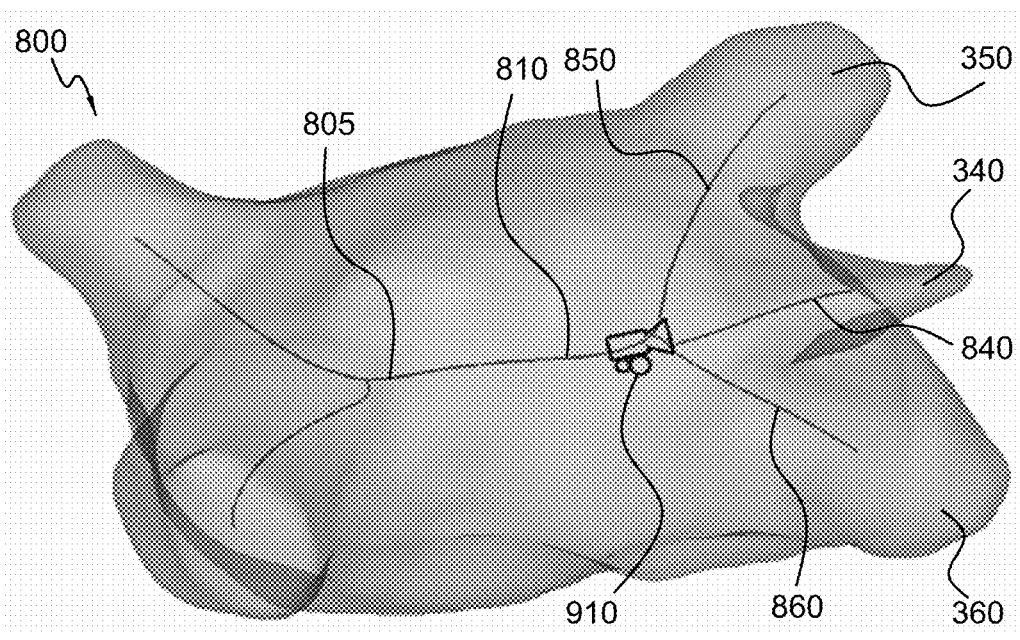
FIG. 10A illustrates an imaging device positioned within a left atrium to obtain a view of the left superior pulmonary vein (LSPV), left inferior pulmonary vein (LIPV), and left atrial appendage (LAA) from inside the cardiac chamber in accordance with a disclosed embodiment of the present application.
Figure 10B:
FIG. 10B illustrates an image of the LSPV, LIPV, and LAA from inside the cardiac chamber obtained from the imaging device illustrated in FIG. 10A.

FIG. 10A illustrates an exemplary embodiment of an imaging device 910 positioned within a left atrium 310 along the main axis 810 of the skeleton axis 805 adjacent a bifurcation junction of the LSPV axis 840, LIPV axis 850, and LAA axis 860 to obtain a view of the LSPV 840, LIPV 850, and LAA 860 from inside the cardiac chamber. FIG. 10B illustrates an image of the LSPV 840, LIPV 850, and LAA 860 from inside the cardiac chamber obtained from imaging device 910 illustrated in FIG. 10A.

Figure 11A:
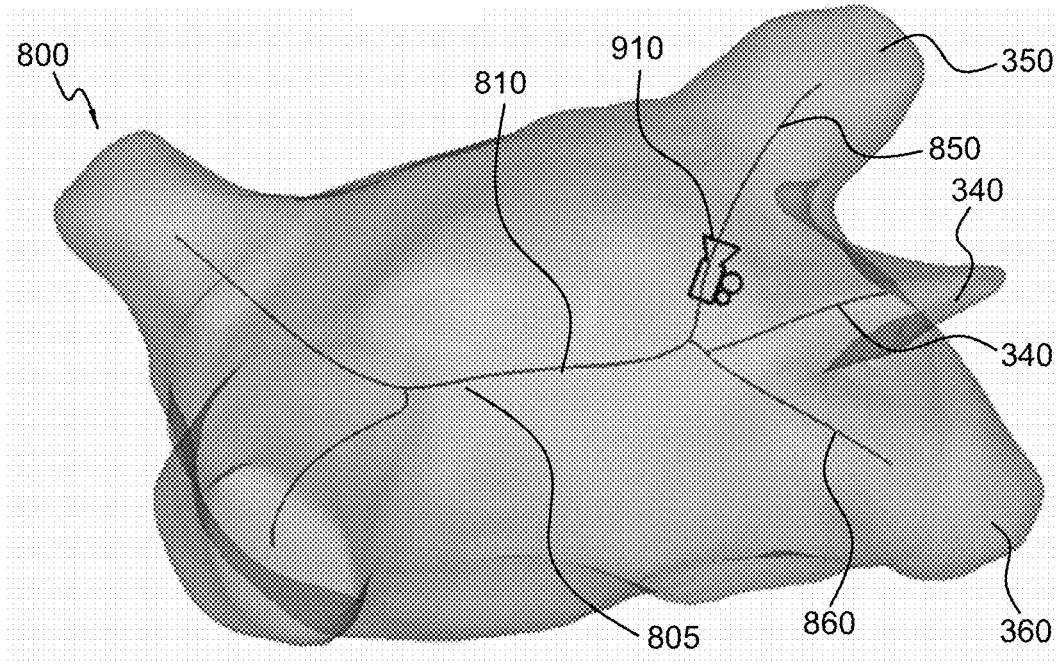
FIG. 11A illustrates an imaging device positioned within a left atrium to obtain a view of the LIPV from inside the LIPV in accordance with a disclosed embodiment of the present application.
Figure 11B:
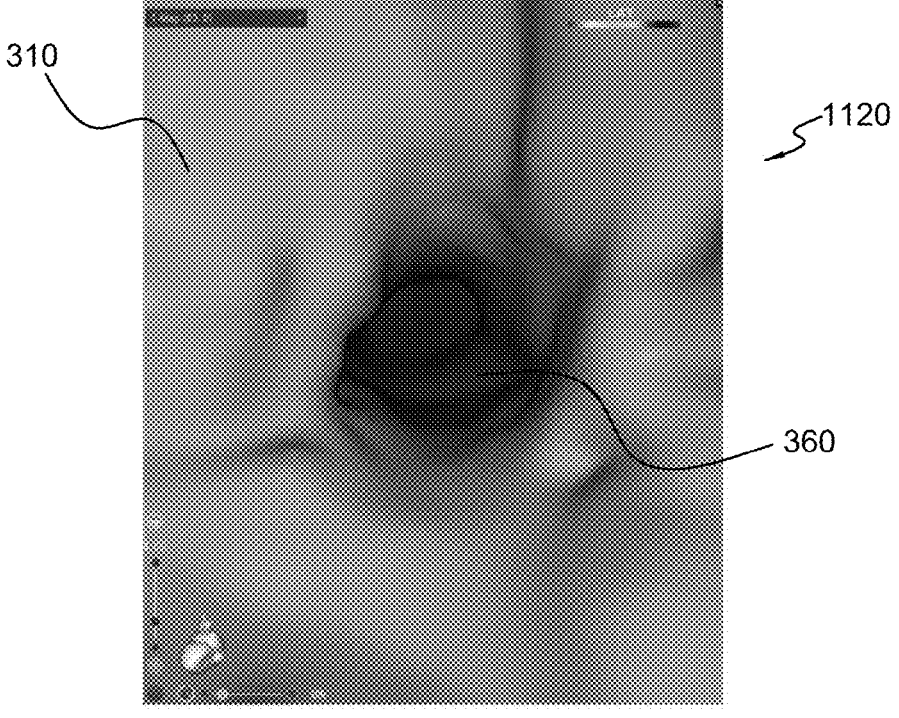
FIG. 11B illustrates an image of the LIPV from inside the LIPV obtained from the imaging device illustrated in FIG. 11A.

FIG. 11A illustrates an exemplary embodiment of an imaging device 910 positioned within a left atrium 310 along the LIPV axis 850 of the skeleton axis 805 to obtain a view of the LIPV 350 from inside the LIPV 350. FIG. 11B illustrates an image of the LIPV 850 from inside the LIPV obtained from imaging device 910 illustrated in FIG. 11A.

At step 740, the obtained image data is preferably communicated to the processing device, such as processor 244, to generate a 3D EP map of the cardiac chamber or cardiac area of interest from within the EP map with a complete visualization of the cardiac location of interest.

At step 750, the generated 3D EP map can optionally be displayed on a display, such as display 227 (FIG. 2).

While FIGS. 5 and 7 relate to exemplary processes for to identify optimal areas for placement of an imaging device, such as imaging device 241, within a cardiac chamber to generate a three-dimensional (3D) view of the cardiac chamber or cardiac area of interest from within the chamber or EP map utilizing the EP mapping system 200 described herein, one of ordinary skill in the art will readily understand that the disclosed processes are not limited and can be applied to visualize other cardiac structures or body organs.

The subject matter disclosed herein for improved cardiac visualization provides a more comprehensive view of a cardiac chamber or cardiac area of interest to assist cardiac procedures, such as an ablation procedure, compared to conventional techniques. For example, the improved cardiac visualization system, method, and techniques disclosed herein reduce or eliminate obscured geometry when viewing an EP map, and reduce or avoid the tedious and time consuming steps of rotation and zooming an EP map to visualize the entire cardiac area of interest.

In an embodiment of the subject matter disclosed herein, a physician or technician can choose the methodology for generating a 3D EP map of the cardiac chamber or cardiac area of interest from within the EP map utilizing the 3D art gallery algorithm or skeleton axis algorithm disclosed herein. For example, and without limitation, if having minimal number of views to see the whole chamber is an important factor, then the art gallery algorithm may be selected. However, if viewing all cardiac areas of interest for ablation is an important factor, then the skeleton algorithm may be selected.

It should be understood that many variations are possible based on the disclosure herein. Although features and elements are described above in particular combinations, each feature or element can be used alone without the other features and elements or in various combinations with or without other features and elements. Similarly, although process steps are described above in a particular order, the steps can be performed in other desirable orders.

The methods, processes and/or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

Certain terminology is used in the description herein for convenience only and is not limiting. The words "right," "left," "top," "bottom," "front," and "back" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Further exemplary embodiments herein may be formed by supplementing an embodiment with one or more element from any one or more other embodiment herein, and/or substituting one or more element from one embodiment with one or more element from one or more other embodiment herein.

It is understood, therefore, that the disclosed subject matter is not limited to the particular embodiments disclosed, but is intended to cover all modifications which are within the spirit and scope of the invention as defined by the appended claims; the above description; and/or shown in the attached drawings.

What is claimed is:

1. A system for visualizing an ablation site for a cardiac structure of interest during a cardiac ablation procedure, the system comprising:
   at least one imaging device; and
   a processor that is communicatively coupled to a memory and the at least one imaging device, wherein the processor is configured to:
   generate an electrophysiological (EP) map based on electrical activity sensed in the cardiac structure of interest;
   receive and store model data of the cardiac structure of interest;
   determine, based on the model data, a plurality of locations within the EP map for positioning the at least one imaging device to image the cardiac structure of interest, wherein the plurality of the locations comprises a minimal number of locations sufficient to create a complete visualization of the ablation site in 3-dimensional (3D) space;
   receive image data from the at least one imaging device positioned at each of the plurality of locations within the cardiac structure of interest during the cardiac ablation procedure;
   generate a 3D view of the ablation site for the cardiac structure of interest by combining the image data and the electrical activity, the 3D view displaying electrophysiological features of the cardiac structure of interest as viewed from inside the cardiac structure of interest; and
   display the 3D view of the ablation site for the cardiac structure of interest during the cardiac ablation procedure.

2. The system of claim 1, wherein the cardiac structure of interest is at least one of:
   a cardiac chamber,
   vein, or
   vein bifurcation.

3. The system of claim 1, wherein the 3D view provides the complete visualization of the ablation site for the cardiac structure of interest in a single view.

4. The system of claim 1, wherein determining the plurality of locations comprises solving a three-dimensional art gallery fixed-point guard placement on a triangulated model of the cardiac structure of interest and mapping visibility subsets of the ablation site to a minimum set-cover problem.

5. The system of claim 1, wherein the plurality of the locations are determined based on a skeleton axis algorithm that generates a skeleton axis of the model data of the cardiac structure of interest.

6. The system of claim 5, wherein at least one of the plurality of locations is along a branch of the skeleton axis that intersects an ablation line of the ablation site.

7. The system of claim 1, wherein the at least one imaging device is an intracardiac probe.

8. A method for visualizing an ablation site for a cardiac structure of interest during a cardiac ablation procedure, the method comprising:
   generating an electrophysiological (EP) map based on electrical activity sensed in the cardiac structure of interest;
   obtaining model data of the cardiac structure of interest;
   determining, based on the model data, a plurality of locations within the EP map for positioning at least one imaging device to image the cardiac structure of interest, wherein the plurality of locations comprises a minimal number of locations sufficient to create a complete visualization of the ablation site in 3-dimensional (3D) space;
   receiving image data from the at least one imaging device positioned at each of the plurality of locations within the cardiac structure of interest during the cardiac ablation procedure;
   generating a 3D view of the ablation site for the cardiac structure of interest by combining the image data and the electrical activity, the 3D view displaying electrophysiological features of the cardiac structure of interest as viewed from inside the cardiac structure of interest; and
   displaying the 3D view of the ablation site for the cardiac structure of interest during the cardiac ablation procedure.

9. The method of claim 8, wherein the cardiac structure of interest is at least one of:
   a cardiac chamber,
   vein, or
   vein bifurcation.

10. The method of claim 8, wherein the 3D view provides the complete visualization of the ablation site for the cardiac structure of interest in a single view.

11. The method of claim 8, wherein determining the plurality of the locations comprises solving a three-dimensional art gallery fixed-point guard placement on a triangulated model of the cardiac structure of interest and mapping visibility subsets of the ablation site to a minimum set-cover problem.

12. The method of claim 8, wherein the plurality of locations are determined based on a skeleton axis algorithm that generates a skeleton axis of the model data of the cardiac structure of interest.

13. The method of claim 12, wherein at least one of the plurality of the locations is positioned along a branch of the skeleton axis that intersects an ablation line of the ablation site.

14. A non-transitory computer readable recording medium storing program instructions for visualizing an ablation site for a cardiac structure of interest during a cardiac ablation procedure, the program instructions when executed by a processor, cause the processor to execute a method comprising:

generating an electrophysiological (EP) map based on electrical activity sensed in the cardiac structure of interest;

obtaining model data of the cardiac structure of interest;

determining, based on the model data, a plurality of locations within the EP map for positioning at least one imaging device to image the cardiac structure of interest, wherein the plurality of the locations comprises a minimal number of locations sufficient to create a complete visualization of the ablation site in 3-dimensional (3D) space;

receiving image data from the at least one imaging device positioned at each of the plurality of the locations within the cardiac structure of interest during the cardiac ablation procedure;

generating a 3D view of the ablation site for the cardiac structure of interest by combining the image data and the electrical activity, the 3D view displaying electrophysiological features of the cardiac structure of interest as viewed from inside the cardiac structure of interest; and displaying the 3D view of the ablation site for the cardiac structure of interest during the cardiac ablation procedure.

15. The method of claim 8, further comprising:

positioning the at least one imaging device at each of the plurality of the locations within the cardiac structure of interest.

16. The non-transitory computer readable recording medium of claim 14, wherein the method further comprises:

positioning the at least one imaging device at each of the plurality of the locations within the cardiac structure of interest.

17. The system of claim 1, wherein:

the cardiac structure of interest comprises a left atrium and pulmonary veins, the ablation site comprises a circumferential lesion set around at least one pulmonary vein ostium, and the processor is further configured to generate the 3D view such that the entire circumferential lesion set is simultaneously visible in a single view without rotating or zooming the electrophysiological map.

18. The method of claim 8, wherein:

the cardiac structure of interest comprises a left atrium and pulmonary veins, the ablation site comprises a circumferential lesion set around at least one pulmonary vein ostium, and the generating the 3D view comprises generating the 3D view such that the entire circumferential lesion set is simultaneously visible in a single view without rotating or zooming the electrophysiological map.

19. The system of claim 4, wherein the fixed-point guard placement is constrained such that candidate guard locations are limited to points along a skeleton (medial) axis of the cardiac structure of interest computed from the model data.

20. The method of claim 11, wherein the fixed-point guard placement is constrained such that candidate guard locations are limited to points along a skeleton (medial) axis of the cardiac structure of interest computed from the model data.

* * * * *